United States Patent
Zino et al.

(10) Patent No.: US 9,721,379 B2
(45) Date of Patent: Aug. 1, 2017

(54) REAL-TIME SIMULATION OF FLUOROSCOPIC IMAGES

(71) Applicant: BIOSENSE WEBSTER (ISRAEL) LTD., Yokneam (IL)

(72) Inventors: Eliahu Zino, Atlit (IL); Gil Zigelman, Haifa (IL); Liav Moshe Adi, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 14/513,343

(22) Filed: Oct. 14, 2014

(65) Prior Publication Data

US 2016/0104312 A1 Apr. 14, 2016

(51) Int. Cl.

| | |
|---|---|
| *G06T 15/00* | (2011.01) |
| *G06T 15/20* | (2011.01) |
| *A61B 6/12* | (2006.01) |
| *A61B 6/00* | (2006.01) |
| *G06T 7/00* | (2017.01) |
| *G09B 23/30* | (2006.01) |
| *A61B 19/00* | (2006.01) |
| *G06K 9/46* | (2006.01) |
| *G06T 1/60* | (2006.01) |

(Continued)

(52) U.S. Cl.
CPC ............... *G06T 15/20* (2013.01); *A61B 6/12* (2013.01); *A61B 6/4441* (2013.01); *A61B 6/485* (2013.01); *A61B 6/487* (2013.01); *A61B 6/50* (2013.01); *A61B 6/503* (2013.01); *A61B 6/52* (2013.01); *A61B 6/547* (2013.01); *A61B 19/50* (2013.01); *A61B 34/20* (2016.02); *G06K 9/46* (2013.01); *G06T 1/60* (2013.01); *G06T 7/0012* (2013.01); *G06T 15/08* (2013.01); *G09B 23/30* (2013.01); *A61B 2019/505* (2013.01); *A61B 2019/507* (2013.01); *G06T 2207/10121* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |

(Continued)

FOREIGN PATENT DOCUMENTS

| | | |
|---|---|---|
| EP | 2722018 A2 | 4/2014 |
| WO | WO 96/05768 A1 | 2/1996 |

OTHER PUBLICATIONS

Extended European Search Report EP15189512 Issued Mar. 4, 2016.

*Primary Examiner* — Andrew G Yang
(74) *Attorney, Agent, or Firm* — Louis J. Capezzuto

(57) ABSTRACT

A method includes registering a first coordinate system of a fluoroscopic imaging system and a second coordinate system of a magnetic position tracking system. A three-dimensional (3D) map of an organ of a patient is computed using the magnetic position tracking system. A field-of-view (FOV) of the fluoroscopic imaging system in the second coordinate system is calculated using the registered first and second coordinate systems. Based on the 3D map and the calculated FOV, a two-dimensional (2D) image that simulates a fluoroscopic image that would be generated by the fluoroscopic imaging system is created, and the 2D image that simulates the fluoroscopic image is displayed.

14 Claims, 2 Drawing Sheets

(51) Int. Cl.
*A61B 34/20* (2016.01)
*G06T 15/08* (2011.01)

(56) References Cited

U.S. PATENT DOCUMENTS

| | | |
|---|---|---|
| 6,484,118 B1 | 11/2002 | Govari |
| 6,618,612 B1 | 9/2003 | Acker et al. |
| 6,690,963 B2 | 2/2004 | Ben-Haim et al. |
| 7,327,872 B2 | 2/2008 | Vaillant et al. |
| 8,515,527 B2 | 8/2013 | Vaillant et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0184006 A1* | 8/2006 | Chen ............... A61B 6/12 600/416 |
| 2007/0225593 A1* | 9/2007 | Porath ............. A61B 5/06 600/423 |
| 2009/0040224 A1* | 2/2009 | Igarashi .......... G06T 19/00 345/427 |
| 2010/0022874 A1 | 1/2010 | Wang et al. |
| 2012/0289825 A1* | 11/2012 | Rai ................. A61B 6/463 600/425 |
| 2013/0272592 A1* | 10/2013 | Eichler ........... A61B 6/547 382/131 |
| 2014/0037173 A1* | 2/2014 | Gum ............... A61N 5/1049 382/131 |
| 2014/0058407 A1* | 2/2014 | Tsekos ............ A61B 19/50 606/130 |

\* cited by examiner

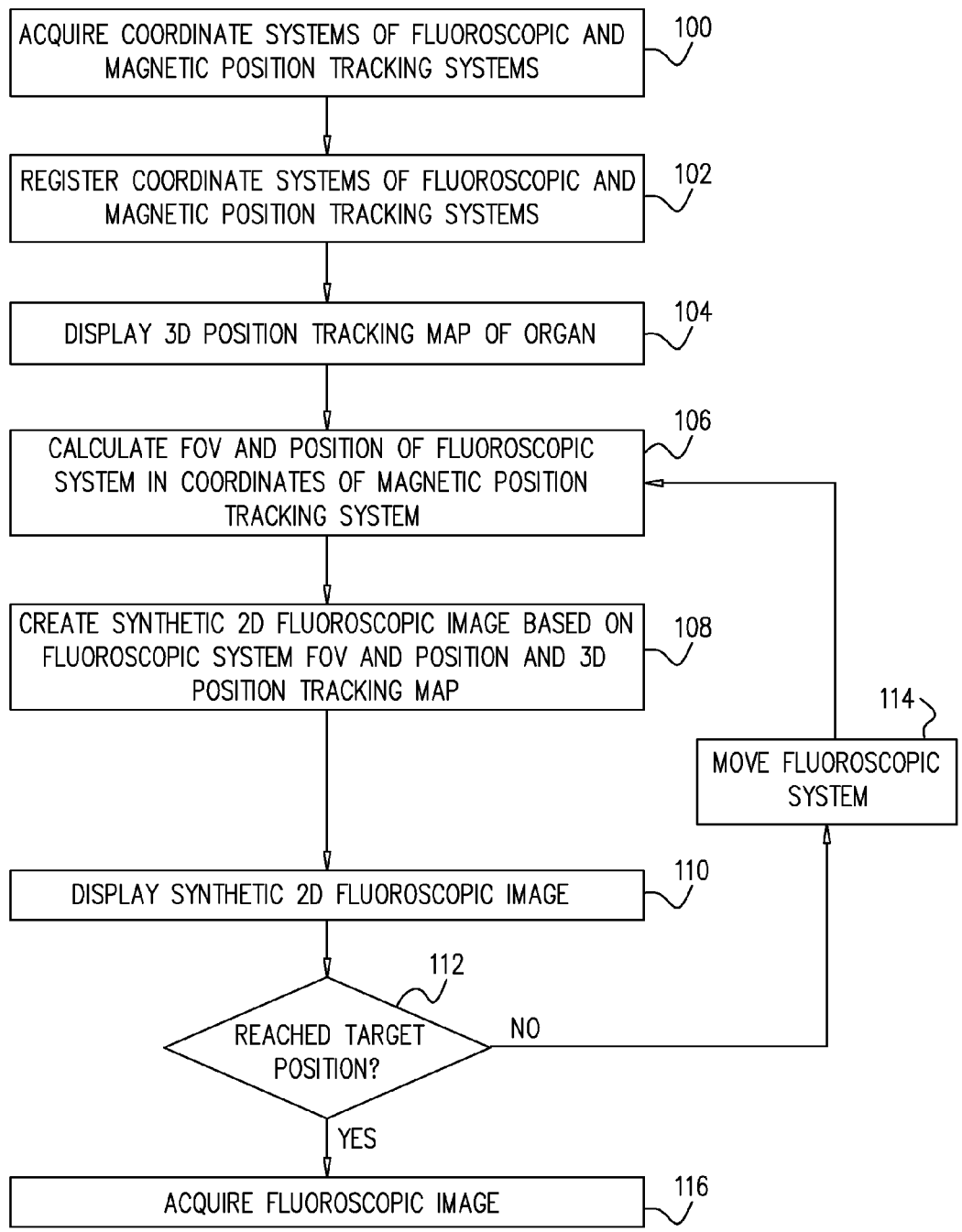

_US 9,721,379 B2_

REAL-TIME SIMULATION OF FLUOROSCOPIC IMAGES

FIELD OF THE INVENTION

The present invention relates generally to medical imaging, and particularly to methods and systems for real-time simulation of fluoroscopic images during medical procedures.

BACKGROUND OF THE INVENTION

Real-time (RT) imaging, such as fluoroscopic imaging, is often used in minimally-invasive medical procedures, sometimes in conjunction with various three-dimensional (3D) imaging modalities. Several techniques deal with registration of RT images with 3D models and 3D maps of patient organs. For example, U.S. Patent Application Publication 2010/0022874, whose disclosure is incorporated herein by reference, describes an image guided navigation system that comprises a memory, a locator, a processor and a display. The memory stores a plurality of CT images and a software program. The locator is capable of indicating a direction to a surgical area, and the indicated direction of the locator is defined as a first direction. The processor is electrically connected to the memory and the locator. At least one corresponding image corresponding to the first direction is obtained from the plurality of CT images by the processor executing the software program. The at least one corresponding image comprises at least one simulated fluoroscopic image. The display is capable of showing the at least one corresponding image.

U.S. Pat. No. 8,515,527, whose disclosure is incorporated herein by reference, describes a method and an apparatus for registering 3D models of anatomical regions of a heart and a tracking system with projection images of an interventional fluoroscopic system.

U.S. Pat. No. 7,327,872, whose disclosure is incorporated herein by reference, describes a method and a system for registering 3D models with projection images of anatomical regions. A first image acquisition system of a first modality employing a catheter at an anatomical region of a patient is configured to produce a first image of the anatomical region using fluoroscopy, the first image comprising a set of fluoroscopy projection images. A second image acquisition system of a second different modality is configured to generate a 3D model of the anatomical region. An anatomical reference system is common to both the first and second image acquisition systems. A processing circuit is configured to process executable instructions for registering the 3D model with the fluoroscopy image in response to the common reference system and discernible parameters associated with the catheter in both the first and second image acquisition systems.

SUMMARY OF THE INVENTION

An embodiment of the present invention that is described herein provides a method including registering a first coordinate system of a fluoroscopic imaging system and a second coordinate system of a magnetic position tracking system. A three-dimensional (3D) map of an organ of a patient is computed using the magnetic position tracking system. A field-of-view (FOV) of the fluoroscopic imaging system in the second coordinate system is calculated using the registered first and second coordinate systems. Based on the 3D map and the calculated FOV, a two-dimensional (2D) image that simulates a fluoroscopic image that would be generated by the fluoroscopic imaging system is created, and the 2D image that simulates the fluoroscopic image is displayed.

In some embodiments, the method includes creating the 2D image without applying radiation by the fluoroscopic imaging system. In other embodiments, the method includes displaying the 2D image and the 3D map in different display windows. In yet other embodiments, the method includes displaying the 2D image in a sub-window of a display window used for displaying the 3D map.

In an embodiment, the method includes identifying anatomical features of the organ in the 3D map and simulating, based on the calculated FOV, a projection of the anatomical features in the 2D image. In another embodiment, the method includes identifying a medical probe in the 3D map, and displaying the medical probe in the 2D image. In an embodiment, computing the 3D map includes importing into the 3D map one or more objects acquired using an imaging modality other than magnetic position tracking.

There is additionally provided, in accordance with an embodiment of the present invention, a system including a memory and a processor. The memory is configured to store a three-dimensional (3D) map of an organ of a patient, which is produced by a magnetic position tracking system. The processor is configured to register a first coordinate system of a fluoroscopic imaging system and a second coordinate system of the magnetic position tracking system, to compute the 3D map using the magnetic position tracking system, to calculate a field-of-view (FOV) of the fluoroscopic imaging system in the second coordinate system using the registered first and second coordinate systems, to create a two-dimensional (2D) image that simulates a fluoroscopic image that would be generated by the fluoroscopic imaging system based on the 3D map and the calculated FOV, and to display the 2D image that simulates the fluoroscopic image.

The present invention will be more fully understood from the following detailed description of the embodiments thereof, taken together with the drawings in which:

BRIEF DESCRIPTION OF THE DRAWINGS

FIG. 2 is a flow chart that schematically illustrates a method for creating a simulated two-dimensional (2D) fluoroscopic image, in accordance with an embodiment of the present invention.

DETAILED DESCRIPTION OF EMBODIMENTS

Overview

Figure 1:
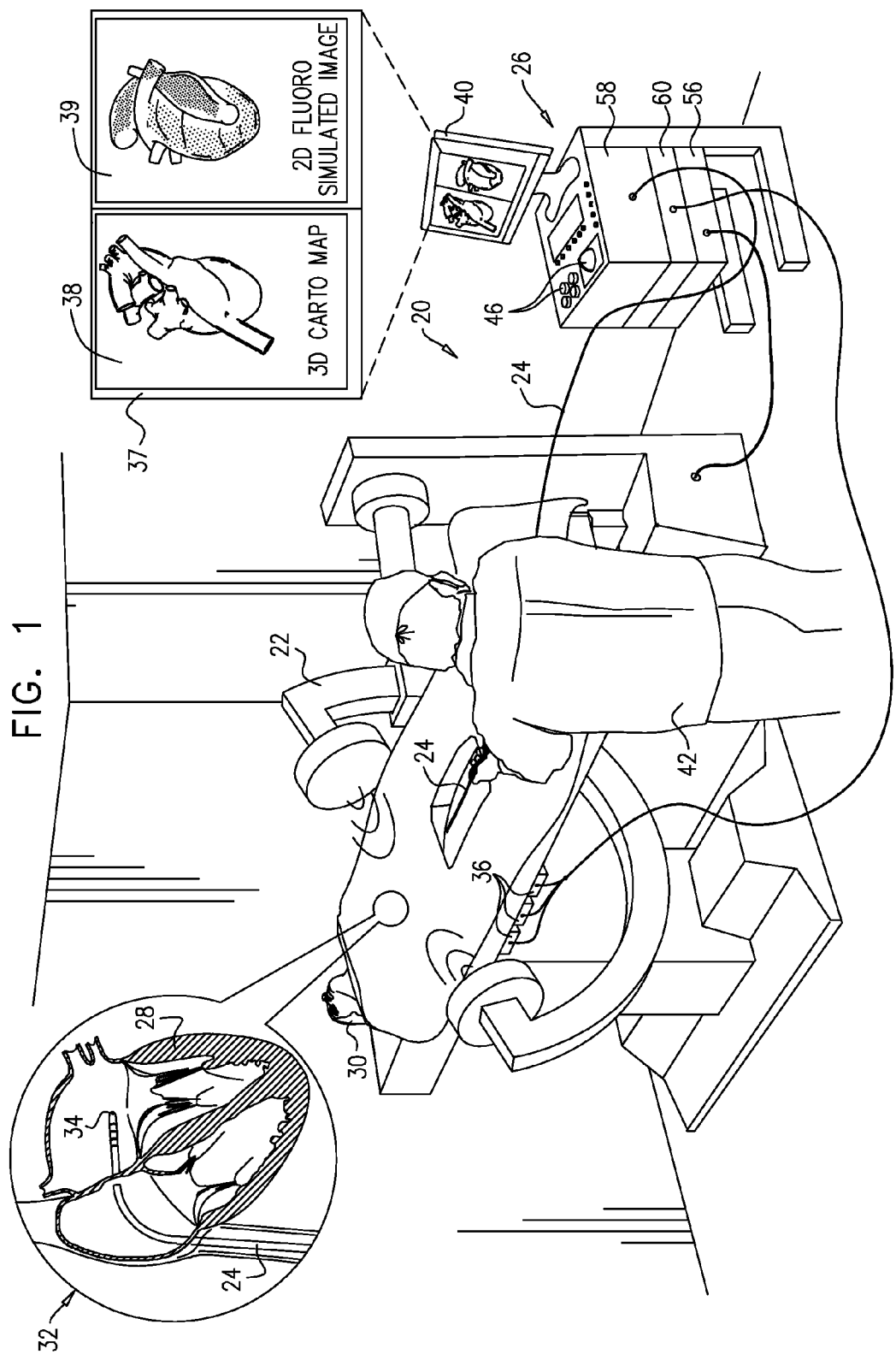
FIG. 1 is a schematic pictorial illustration of a fluoroscopic imaging system and a magnetic position tracking system, in accordance with an embodiment of the present invention.

Minimally-invasive medical procedures often use imaging capabilities, such as magnetic position tracking maps. For example, Biosense-Webster, Inc. (Diamond Bar, Calif.) provides the CARTO™ system, used for visualizing a catheter in a patient heart using magnetic-field position tracking. In some cases, there is a need for a real-time (RT) fluoroscopic image of the same location, in parallel to the magnetic position tracking map. Fluoroscopic imaging, however, exposes the patient and staff to potentially-hazardous doses of X-ray radiation. In practice, the Field-Of-View (FOV) of the fluoroscopic system is often narrow, and a considerable portion of X-ray radiation is applied when attempting to position the fluoroscopic system to image the desired location in a patient's body.

Embodiments of the present invention that are described herein provide improved methods and systems for jointly operating a fluoroscopic system and a magnetic position tracking system. In some embodiments, a processor of the magnetic position tracking system registers the coordinate systems of the fluoroscopic system and the magnetic position tracking system, and calculates the FOV of the fluoroscopic system in the coordinate system of the magnetic position tracking system. Using this information, the processor creates a two-dimensional (2D) image that simulates a fluoroscopic image that would be generated if the fluoroscopic imaging system were to be activated at this point.

The 2D image is based on the computed 3D map of the magnetic position tracking system, and does not originate from the fluoroscopic imaging system at all. In the context of the present patent application and in the claims, the term "3D map" refers to a 3D model that is obtained using the magnetic position tracking system as well as possibly imported segmented objects from additional imaging modalities such as Computerized Tomography (CT), Magnetic Resonance Imaging (MRI) or any other suitable imaging techniques. Such a model may comprise various objects, such as contours and anatomical features of the imaged organ, medical probes or instruments in or around the organ, and/or any other suitable object. Any such object of the 3D model may be used for producing the 2D image and/or may appear in the 2D image.

Even though the 2D image is not produced by the fluoroscopic imaging system, the 2D image is visually similar to a fluoroscopic image, and encompasses the same FOV that would have been viewed by the fluoroscopic imaging system if it were active. As a result, the physician can be provided with a real-time display that appears like fluoroscopic imaging but does not involve irradiating the patient.

The disclosed technique may assist the physician to position the fluoroscopic system FOV in the target position, without exposing the patient and medical staff to X-ray radiation, and to accurately position the fluoroscopic system FOV on target with high speed and accuracy. The fluoroscopic system is typically activated only after its FOV is positioned correctly.

System Description

FIG. 1 is a schematic pictorial illustration of a fluoroscopic imaging system 22 and a magnetic position tracking system 20 during a minimally invasive cardiac procedure, in accordance with an embodiment of the present invention. Fluoroscopic imaging system 22 is connected to magnetic position tracking system 20 via an interface 56. System 20 comprises a console 26, and a catheter 24, which has a distal end 34 as shown in an insert 32 of FIG. 1.

A cardiologist 42 (or any other user) navigates catheter 24 in a patient's heart 28, until distal end 34 reaches the desired location in this organ, and then cardiologist 42 performs a medical procedure using distal end 34. In other embodiments, the disclosed techniques can be used with procedures that are performed in any other organ, and instead of cardiologist 42, any suitable user (such as a pertinent physician, or an authorized technician) can operate the system.

This method of position tracking is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Pat. No. Application Publications 2002/0065455 A1, 2003/0120150 A1 and 2004/0068178 A1, whose disclosures are all incorporated herein by reference.

Console 26 comprises a processor 58, a driver circuit 60, and interface 56 to system 22, input devices 46, and a display 40. Driver circuit 60 drives magnetic field generators 36, which are placed at known positions below a patient's 30 torso. In case a fluoroscopic image is needed, cardiologist 42 uses input devices 46 and a suitable Graphical User Interface (GUI) on display 40 to request a fluoroscopic image in patient's heart 28.

In some embodiments, display 40 comprises two windows, as shown in an insert 37 of FIG. 1. A 3D CARTO map 38 window displays a 3D magnetic position tracking map of an organ at the position of distal end 34. A simulated 2D fluoroscopic image 39 window displays a simulated 2D fluoroscopic image at the position of system 22.

In an embodiment, the simulated 2D fluoroscopic image is created based on the 3D magnetic position tracking map and not based on parameters of system 22, as described herein below in details.

In the example of FIG. 1 catheter 24 is present. However, once systems 20 and 22 are registered, the presence of the catheter is not mandatory. Registration may be performed, for example, using a special registration jig and can be done before or after the catheter is inserted into the patient. In an embodiment, if the catheter is positioned within the covered frame area, then it appears in map 38 and in image 39.

In another embodiment, cardiologist 42 may decide to exclude catheter 24 or any other object from image 39 as it is a simulated image. Such decisions may also be taken automatically by the system. In other words, processor 58 may filter the objects that are displayed in the simulated 2D image. Objects that can be shown or hidden may comprise, for example, tags, maps, catheters and/or imported segmented images, among others.

The configuration of system 20 shown in FIG. 1 is an example configuration, which is chosen purely for the sake of conceptual clarity. In alternative embodiments, any other suitable configuration can be used for implementing the system. Certain elements of system 20 can be implemented using hardware, such as using one or more Application-Specific Integrated Circuits (ASICs) or Field-Programmable Gate Arrays (FPGAs) or other device types. Additionally or alternatively, certain elements of system 20 can be implemented using software, or using a combination of hardware and software elements.

Processor 58 typically comprises a general-purpose computer, which is programmed in software to carry out the functions described herein. The software may be downloaded to the computer in an electronic form, over a network, for example, or it may, alternatively or additionally, be provided and/or stored on non-transitory tangible media, such as magnetic, optical, or electronic memory.

Creation of a Simulated 2D Fluoroscopic Image

In the example presented in FIG. 1, processor 58 of system 20 displays on display 40 a 3D map of patient's heart 28 comprising distal end 34, so cardiologist 42 knows the exact location of distal end 34 with respect to the pertinent area in heart 28. During a minimally-invasive medical procedure, cardiologist 42 may need fluoroscopic images in the vicinity of distal end 34. The embodiments described herein fulfill the need for minimizing X-ray irradiation while acquiring a 3D fluoroscopic image.

Conventionally, in case a fluoroscopic image is needed, cardiologist 42 defines the desired area by positioning system 22 to point the desired location and then activating system 22 to irradiate X-rays in order to position the fluoroscopic system to image the desired area of heart 28. Typically, the Field-Of-View (FOV) of system 22 is often narrow and may not actually cover the desired area of heart 28. In such cases, cardiologist 42 has to reposition system 22 and re-irradiate X-rays to reach the desired location. This process exposes the patient and medical staff to excess X-ray radiation.

In some embodiments, the presented technique shows on display 40 two images (typically but not necessarily in two windows): 3D CARTO map 38, showing a 3D position tracking map of distal end 34 within heart 28, and image 39 at the position of system 22.

In a typical flow, processor 58 of system 20 calculates a FOV that would be irradiated by fluoroscopic imaging system 22 in the coordinate system of magnetic position tracking system 20, based on a registration of the coordinate systems of system 22 and system 20. Subsequently, processor 58 uses the calculated FOV of system 22 in the coordinate system of magnetic position tracking system 20, and 3D map 38, to create a simulated 2D image (shown as image 39 in FIG. 1) without irradiating X-rays by system 22.

As demonstrated in FIG. 1, fluoroscopic imaging system 22 is positioned at some arbitrary angle relative to the coordinate system of magnetic position tracking system 20. Nevertheless, simulated 2D image 39 is displayed as if taken from the position of fluoroscopic imaging system 22 or from any other selected angle regardless the current position of system 22, even though it is calculated from the 3D map of position tracking system 20.

In an embodiment cardiologist 42 may move system 22 relative to patient 30 in the same way that it is performed during a conventional procedure, but without irradiating patient 30. As system 22 moves, processor 58 continuously displays simulated 2D images that reflect the changing FOV of system 22 in real time.

In some embodiments the processor is using anatomical features of the heart, which appear as elements in the 3D map of the magnetic position tracking system, to create the simulated 2D fluoroscopic image. For example, a 3D map of an interface between an atrium and a ventricle can be used to create image 39.

Note that image 39 is created without using radiation from system 22, and it is based on map 38. Accordingly, in case the FOV of system 22 falls outside 3D map 38 of system 20, image 39 would not show a simulated image of its current position since it does not have the attributes provided by map 38 to create the required simulated image.

In an embodiment, cardiologist 42 uses the simulated 2D fluoroscopic image and the 3D position tracking map to position system 22 at the desired location and then, to apply X-ray by system 22 and acquire a real fluoroscopic image.

Typically, map 38 comprises anatomical features of the organ in question, and optionally additional elements in the FOV of map 38 such as catheters. In cardiac imaging, such objects may comprise, for example, cardiac chambers, valves, arteries, and other objects. In some embodiments processor 58 identifies such anatomical features (e.g., tissue types, anatomical landmarks) in map 38 and calculates how they would appear in 2D when viewed from the FOV of system 22 to create image 39 from map 38.

Image 39 is simulated from map 38, however typically it is visually similar to a real fluoroscopic image (e.g., same grey scale, same resolution, same look-and-feel), even though it does not originate from nor based on imaging attributes from system 22. In some embodiments, image 39 may have enhancements over the radiation-based fluoroscopic image, such as higher resolution, display in color, and additional simulated enhancements.

In the example of FIG. 1, the 3D map and the 2D image are displayed in separate display windows. In an alternative embodiment, the simulated 2D image is displayed as a "picture-in-picture," i.e., in a sub-window of the window used for displaying the 3D map. In an embodiment, the 2D image is refreshed in response to the physician pressing a pedal or other input device of the magnetic position tracking system. Such a pedal has a similar look-and-feel to the pedal that is commonly used to acquire fluoroscopic images, but in the present example is part of system 20, not 22.

FIG. 2 is a flow chart that schematically illustrates a method for creating a simulated two-dimensional (2D) fluoroscopic image 39, in accordance with an embodiment of the present invention. The method begins at a coordinate acquisition step 100, in which processor 58 acquires the coordinate systems of system 22 and system 20. At a coordinate system registration step 102, processor 58 registers the coordinate systems of system 22 and system 20, in order to match positions of a pertinent organ in patient 30 at both systems.

At a position tracking presentation step 104, processor 58 displays 3D position tracking map 38 of a given organ of patient 30 on display 40. In an embodiment, the organ is heart 28, but may be any pertinent organ of patient 30 in other embodiments. At a FOV calculation step 106, processor 58 uses a registration of the coordinate systems of system 22 and system 20 to calculate the FOV of system 22 in the coordinate system of magnetic position tracking system 20. In some embodiments, the position of system 22 is measured by position sensors attached to a radiation head of system 22. In alternative embodiments, TCP/IP communication with system 22 can be used to extract geometrical information and detector settings. Such alternative embodiments allows to use the correct magnification ("zoom"), which may not be applicable while using sensors.

At a simulation step 108, processor 58 uses the calculated FOV of fluoroscopic imaging system 22 in the coordinate system of magnetic position tracking system 20, and 3D CARTO map 38, to create a simulated 2D fluoroscopic image (image 39 in FIG. 1) without irradiating X-rays by system 22 and without using any radiation parameters of system 22.

At a 2D display step 110, processor 58 displays image 39 on display 40.

In some embodiments image 39 is displayed in a window near map 38 as shown in insert 37 of FIG. 1. In other embodiments image 39 is displayed at the same window of map 38, side by side or at any other suitable manner. At a decision step 112, cardiologist 42 examines image 39 with respect to map 38 and decides whether system 22 is positioned at the desired location to acquire a real fluoroscopic image. If cardiologist 42 decides that system 22 is positioned at the desired location, he/she uses input devices 46 and GUI on display 40 to command system 22 (via processor 58 and interface 56) to acquire a fluoroscopic image, at an image acquisition step 116. In other embodiments the cardiologist may count on the simulated image to avoid radiation, or may use old fluoroscopic images as a reference and use the simulated image for tracking the catheter.

Note that all the method steps prior to step 116 are typically performed while fluoroscopic system 22 does not emit X-ray radiation.

If cardiologist 42 decides that system 22 is not positioned at the desired location, the cardiologist repositions the fluoroscopic system relative to the patient, at a repositioning step 114.

At this point, in various embodiments, the method may loop back to various previous stages of the process. In an embodiment where system 22 is tracked using TCP/IP communication with system 22, the simulated image can be displayed during the motion of the radiation head of system 22.

In other embodiments the flow may loop back to position tracking presentation step 104 or to coordinate acquisition step 100, according to the nature of the source of the registration error of system 22 with respect to patient 30 and magnetic position tracking system 20

Although the embodiments described herein refer mainly to cardiac imaging using fluoroscopy and magnetic position tracking, in alternative embodiments the disclosed techniques may be used with other imaging techniques, such as Magnetic Resonance Imaging (MRI), and applied on other human organs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
    registering a first coordinate system of a fluoroscopic imaging system and a second coordinate system of a magnetic position tracking system;
    computing a three-dimensional (3D) map of an organ of a patient using the magnetic position tracking system;
    using the registered first and second coordinate systems, calculating a field-of-view (FOV) of the fluoroscopic imaging system in the second coordinate system;
    creating from the 3D map a two-dimensional (2D) image that simulates a fluoroscopic image that would be generated by the fluoroscopic imaging system if radiation was applied to a subject by the fluoroscopic imaging system at the calculated FOV; and
    displaying the 2D image that simulates the fluoroscopic image.

2. The method according to claim 1, wherein creating the 2D image is performed without applying radiation by the fluoroscopic imaging system.

3. The method according to claim 1, wherein displaying the 2D image comprises displaying the 2D image and the 3D map in different display windows.

4. The method according to claim 1, wherein displaying the 2D image comprises displaying the 2D image in a sub-window of a display window used for displaying the 3D map.

5. The method according to claim 1, wherein creating the 2D image comprises identifying anatomical features of the organ in the 3D map and simulating, based on the calculated FOV, a projection of the anatomical features in the 2D image.

6. The method according to claim 1, wherein creating the 2D image comprises identifying a medical probe in the 3D map, and displaying the medical probe in the 2D image.

7. The method according to claim 1, wherein computing the 3D map comprises importing into the 3D map one or more objects acquired using an imaging modality other than magnetic position tracking.

8. A system, comprising:
    a memory, which is configured to store a three-dimensional (3D) map of an organ of a patient, which is produced by a magnetic position tracking system; and
    a processor, which is configured to register a first coordinate system of a fluoroscopic imaging system and a second coordinate system of the magnetic position tracking system, to compute the 3D map using the magnetic position tracking system, to calculate a field-of-view (FOV) of the fluoroscopic imaging system in the second coordinate system using the registered first and second coordinate systems, to create a two-dimensional (2D) image from the 3D map that simulates a fluoroscopic image that would be generated by the fluoroscopic imaging system if radiation was applied to a subject by the fluoroscopic imaging system at the calculated FOV, and to display the 2D image that simulates the fluoroscopic image that would be generated if radiation was applied to a subject with the fluoroscopic imaging system at the position.

9. The system according to claim 8, wherein the processor is configured to create the 2D image without applying radiation by the fluoroscopic imaging system.

10. The system according to claim 8, wherein the processor is configured to display the 2D image and the 3D map in different display windows.

11. The system according to claim 8, wherein the processor is configured to display the 2D image in a sub-window of a display window used for displaying the 3D map.

12. The system according to claim 8, wherein the processor is configured to create the 2D image by identifying anatomical features of the organ in the 3D map and simulating, based on the calculated FOV, a fluoroscopic projection of the anatomical features in the 2D image.

13. The system according to claim 8, wherein the processor is configured to identify a medical probe in the 3D map, and to display the medical probe in the 2D image.

14. The system according to claim 8, wherein the processor is configured to import into the 3D map one or more objects acquired using an imaging modality other than magnetic position tracking.

* * * * *